(12) United States Patent
Spitznagel

(10) Patent No.: US 9,751,224 B2
(45) Date of Patent: Sep. 5, 2017

(54) FORCEPS

(71) Applicant: KARL KLAPPENECKER GMBH & CO. KG, Tuttlingen-Nendingen (DE)

(72) Inventor: Bernhard Spitznagel, Seitingin-Oberflacht (DE)

(73) Assignee: KARL KLAPPENECKER GMBH & CO. KG, Tuttlingen-Nendingen (DE)

( * ) Notice: Subject to any disclaimer, the term of this patent is extended or adjusted under 35 U.S.C. 154(b) by 87 days.

(21) Appl. No.: 14/895,574

(22) PCT Filed: Jun. 3, 2014

(86) PCT No.: PCT/EP2014/061455
§ 371 (c)(1),
(2) Date: Apr. 1, 2016

(87) PCT Pub. No.: WO2014/195295
PCT Pub. Date: Dec. 11, 2014

(65) Prior Publication Data
US 2016/0257007 A1      Sep. 8, 2016

(30) Foreign Application Priority Data

Jun. 4, 2013   (DE) .................. 10 2013 105 751

(51) Int. Cl.
| | |
|---|---|
| B26B 13/04 | (2006.01) |
| B26B 13/28 | (2006.01) |
| A61B 17/88 | (2006.01) |
| B23D 29/02 | (2006.01) |

(Continued)

(52) U.S. Cl.
CPC .......... *B26B 13/04* (2013.01); *A61B 17/8863* (2013.01); *B23D 29/023* (2013.01); *B26B 13/28* (2013.01); *B26B 29/00* (2013.01); *A61B 2017/00526* (2013.01)

(58) Field of Classification Search
CPC ......... B26B 13/04; B26B 13/28; B26B 29/00; A61L 317/8863
See application file for complete search history.

(56) References Cited

U.S. PATENT DOCUMENTS

| | | |
|---|---|---|
| 103,152 A | 5/1870 | Daniels |
| 4,221,048 A | 9/1980 | Parramore |
| 4,891,883 A | 1/1990 | Mäntele |

(Continued)

FOREIGN PATENT DOCUMENTS

| | | |
|---|---|---|
| DE | 9105152 U1 | 9/1991 |
| DE | 20018390 U1 | 1/2001 |

(Continued)

OTHER PUBLICATIONS

International Search Report for PCT/EP2014/061455 dated Jul. 30, 2014.

*Primary Examiner* — Sean Michalski
(74) *Attorney, Agent, or Firm* — Bachman & LaPointe, PC

(57) ABSTRACT

A forceps, in particular surgical forceps, having at least one handle and a pressure lever which is mounted in a pivotal manner relative to the handle and further having a jaw consisting of two jaw parts, one of which is provided on the handle. A lever arm is to be arranged between the handle and the pressure lever, wherein the lever arm has the second jaw part and pressure can be applied to the lever arm by the pressure lever.

15 Claims, 5 Drawing Sheets

(51) Int. Cl.
    *B26B 29/00*        (2006.01)
    *A61B 17/00*        (2006.01)

(56) References Cited

U.S. PATENT DOCUMENTS

| | | | |
|---|---|---|---|
| 8,713,805 B2* | 5/2014 | Schneider | B26B 13/16 |
| | | | 30/244 |
| 2002/0069537 A1 | 6/2002 | Wenzler | |
| 2011/0131814 A1* | 6/2011 | Musser | A01G 3/02 |
| | | | 30/260 |
| 2014/0053411 A1 | 2/2014 | Merz | |
| 2016/0221199 A1* | 8/2016 | Wong | B26B 13/06 |

FOREIGN PATENT DOCUMENTS

| | | |
|---|---|---|
| DE | 20207785 U1 | 9/2003 |
| DE | 102011001013 A1 | 9/2012 |
| EP | 0321884 B1 | 11/1993 |
| FR | 2389459 A1 | 12/1978 |
| GB | 139528 A | 3/1920 |

* cited by examiner

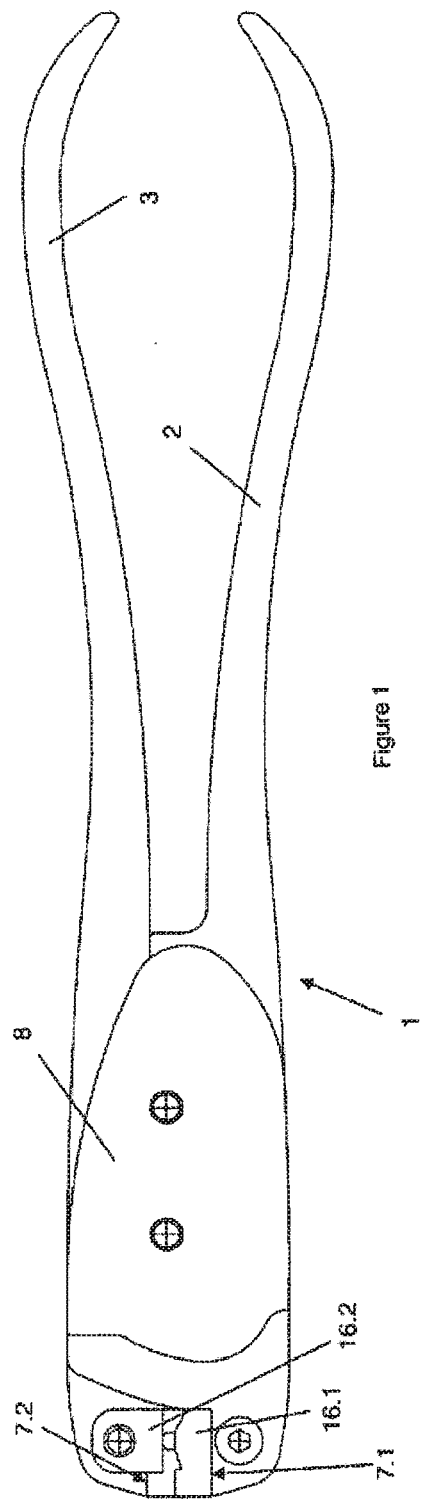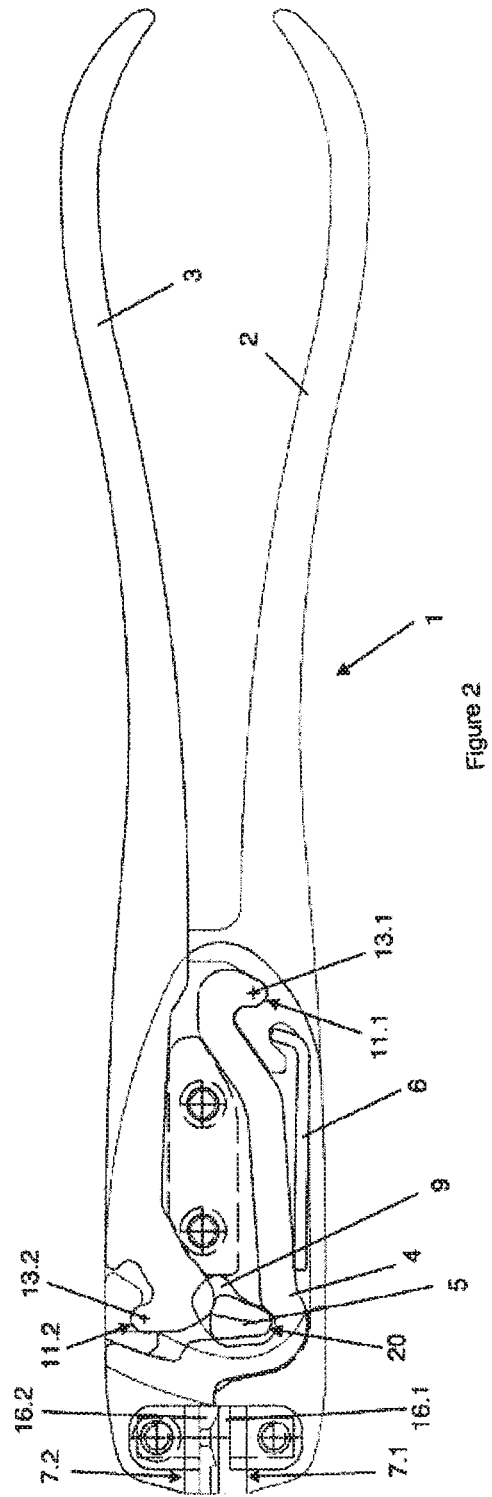

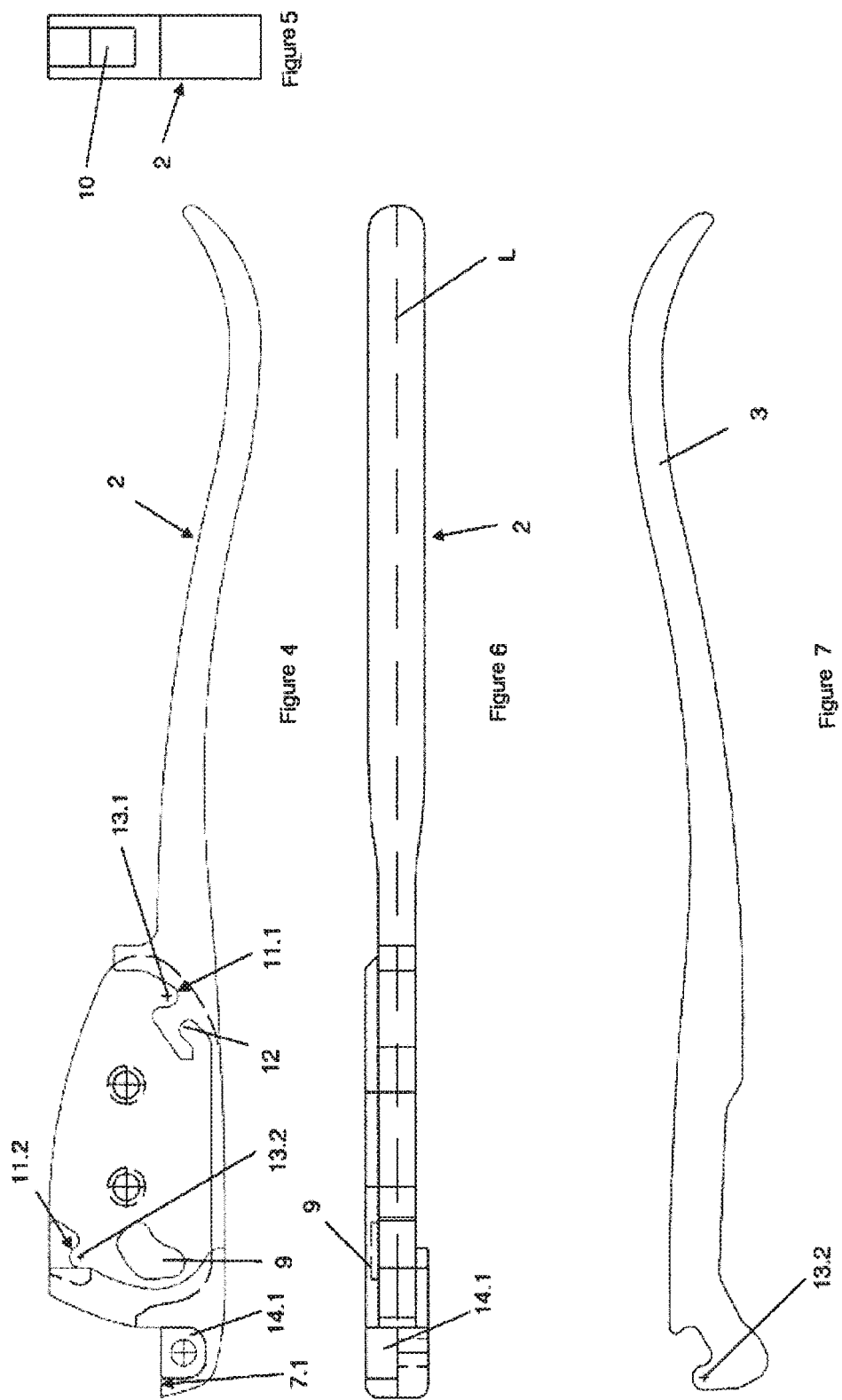

FORCEPS

BACKGROUND OF THE INVENTION

The invention relates to a forceps, in particular a surgical forceps.

Various surgical forceps for cutting implants and/or medical wires are known from the prior art. Since frequently high shearing forces have to be produced in order to cut implants and/or medical wires, said forceps generally have multiple transmission ratios, for example in the form of toggle lever drives. Furthermore, said forceps are generally shaped ergonomically in order to be able to be operated by the operator using one hand.

EP 0 321 884 B1 depicts a forceps for cutting wire, which is provided with a plurality of toggle lever drives connected via bolts. Said toggle lever drives are intended to permit cutting even of thicker wires using one hand. It is disadvantageous, however, that the cutting edges in the open state spread far apart from each other and are not aligned parallel to each other, and therefore there is the possibility that the wire may slide out of the cutting edges when the forceps are pressed together.

A further such forceps having a plurality of joints which form toggle lever drives is depicted in DE 20 207 785 U1. The cutting edges of these forceps have recesses which are conceived for receiving a wire and for preventing slipping. However, in the open state, the cutting edges here are also spread far apart from each other.

In general, the cleaning of the complex devices constitutes a growing problem recently in the sphere of surgical instruments. While the devices become technically evermore elaborate, an ever greater outlay is required for the cleaning thereof. This also applies to the previously depicted forceps from EP 321 884 B1 and DE 20 207 785 U1.

In particular, those partial regions of the forceps which cannot be transferred or can only be transferred conditionally into a sterile state by means of a cleaning process, in particular using cleaning agents, constitute an immense risk.

DE 10 2011 001 013 A1 discloses a forceps for cutting workpieces, in particular made of metal, with at least one forceps limb and a pressure element, which are connected to each other via a fulcrum. The intention here is to assign a cutting element with a cutting jaw to the forceps limb, wherein a base of the forceps jaw and a base of the cutting jaw are arranged in the vicinity of a fulcrum about which the cutting element rotates in the forceps limb. When the pressure element is moved toward the forceps limb, a pressure piece carries along the cutting element such that the latter, guided by a guide pin, rotates about the fulcrum in a guide channel and in a roller cage.

FR 2 389 459 A1 discloses a further forceps in which a ratchet wheel is arranged on a forceps limb so as to be rotatable about an axis of rotation, wherein the rotation is brought about by the other forceps limb. The ratchet wheel has a sliding block which, with the surface thereof, runs off a cutting element on which a jaw part is provided.

A forceps of the abovementioned type is known from GB 139 528 A, wherein a handle part is assigned a pressure lever which is mounted pivotably in relation to the handle part. A jaw part is provided on the handle part. Furthermore, a lever arm is arranged between the handle part and the pressure lever, which lever arm has a second jaw part and is pressurizable by the pressure lever. The lever arm is mounted pivotably in relation to the handle part.

A surgical forceps is known from DE 200 18 390 U1.

It is the object of the present invention to overcome the disadvantages of the prior art. In particular, the intention is to provide a forceps which permits a simply achieved, but high transmission ratio. Furthermore, the intention is to provide a forceps in which the transmission ratio is intended to be formed without fixed connections and which can be used for various purposes.

In addition, tool elements introduced into jaw parts are intended to be aligned at least virtually parallel to one another in the open state. The intention is also to provide a forceps in which the tool elements can be interchanged without a large outlay.

In addition, the intention is to provide a forceps which, without a large outlay, can be cleaned in a cleaning process in such a manner that the forceps is sterile and, furthermore, can be dismantled into individual parts in a simple manner and can be assembled likewise in a simple manner.

SUMMARY OF THE INVENTION

The object is achieved by the features of the present invention wherein, to achieve a high transmission ratio, the rolling body is arranged between the pressure lever and the lever arm. Said rolling body is designed here in such a manner that it makes it possible to transmit a force from the pressure lever to the lever arm. In order to achieve this, the rolling body is guided in a slotted guide. In addition, the lever arm has a preferably concave receptacle for the rolling body. This produces a type of toggle lever which contributes to the high transmission ratio of the forceps. In a typical exemplary embodiment, the rolling body and the resulting toggle lever are arranged in that side of the housing of the handle part which faces the jaw part.

The mounting between handle part and pressure lever and the mounting between lever arm and handle part involve a free mounting. Said mountings are located in a region of the handle part that is formed as part of a housing. In a typical exemplary embodiment, the free mountings are designed in a manner of a joint in the form of a turning joint or turning and sliding joint.

The two free mountings are rolling surfaces which permit pivoting of the pressure lever and of the lever arm. The lever arm and/or the pressure lever here preferably turn about a fulcrum/pivot point. Furthermore, there is also the possibility that the fulcrum/pivot point constitutes a non-punctiform region in which the lever arm and/or the pressure lever can pivot within the housing during actuation of the forceps.

In order to achieve as high a transmission ratio as possible, preferably at least a transmission ratio of 1 to 15, the fulcrum/pivot points of the pressure lever and the lever arm are at as large a distance from each other as possible.

The fulcrum/pivot point of the pressure lever is located here on a side of the pressure lever facing the jaw part. In a typical exemplary embodiment, this end of the pressure lever is inserted into a concave receptacle which is located in the handle part on that side of the housing which faces the jaw part. The concave receptacle furthermore constitutes the rolling surface which, instead of a conventional joint in the form of a bolt or rivet, serves as a bearing for the pressure lever.

The fulcrum/pivot point of the lever arm is located on a side of the lever arm facing away from the jaw part. In a typical exemplary embodiment, that end of the lever arm which faces away from the jaw part is inserted into a concave receptacle which is located in the handle part on that side of the housing which faces away from the jaw part. Here too, the concave receptacle constitutes the rolling surface which, instead of a conventional joint in the form of a bolt or rivet, serves as a bearing for the lever arm.

The effect achieved by the greatest possible distance between the mounting and therefore the fulcrum/pivot point of the lever arm from the jaw part, in addition to the high transmission ratio, is that the jaw parts are aligned virtually parallel to each other even in the open state.

The mountings between handle piece and pressure lever, handle piece and lever arm, pressure lever and rolling body and rolling body and lever arm have similar or the same functions that joints in a conventional forceps have. Therefore, in a typical exemplary embodiment, the concave receptacles are a type of socket while the ends of the lever arm and of the pressure lever are a type of joint head. Similarly, in a typical exemplary embodiment, that side of the rolling body which faces the lever arm is a type of joint head.

The mounting and therefore the fulcrum/pivot point between the pressure lever and the handle piece and the rolling surfaces between the rolling body and the pressure lever and between the rolling body and the lever arm are located, in a typical exemplary embodiment, on that side of the housing of the forceps which faces the jaw part. Thus, in a typical exemplary embodiment, only the mounting and therefore the fulcrum/pivot point between lever arm and handle piece is located on that side of the housing of the forceps which faces away from the jaw part and is therefore further away from the jaw part.

By means of the use of rolling surfaces for the mounting and of the rolling body for forming a toggle lever, the friction within the forceps can be reduced to a small size. As a result, a large force acting on the jaw parts can be produced. Since only a small distance is required in order to produce the force, the forceps can be used and operated using one hand.

Furthermore, in a typical exemplary embodiment, the components in the region of the mountings or of the rolling surfaces generally have unequal geometries, in particular unequal radii. For example, a turning and/or turning and sliding movement can be achieved by the radius of the respective concave receptacles being larger, in a typical exemplary embodiment, than the outside radius of the end of the respective component which is mounted in the receptacle. A rolling movement and therefore little friction is thereby made possible.

The slotted guide for guiding the rolling body is provided in the handle part and/or in a housing cover. The housing cover is suitable for closing the housing which is at least partially represented by the handle part. The housing cover is preferably connected to the handle part by screws. However, the use of a plug-in connection instead of the screw connection is also possible.

Furthermore, the handle part has, within the housing region, a hook-in recess which is suitable for receiving a spring. The jaw of the forceps is opened again by the spring as soon as the pressure lever is no longer pressed in the direction of the handle part.

Furthermore, the handle part has, at the jaw-side end, a recess which is designed as a closed channel in the direction of a longitudinal axis. The longitudinal axis corresponds here approximately to an imaginary connection between the jaw-side end of the handle part and that end of the handle part which faces away from the jaw. In a typical exemplary embodiment, the recess which is designed as a closed channel is suitable for receiving the lever arm which, for this purpose, is pushed into the closed channel from the jaw-side end of the handle piece.

The effect furthermore achieved by the design of the recess as a closed channel is that handle part and therefore the housing have greater stability in this region. In addition, forces acting over the closed contour of the recess can be better conducted away into the handle part.

In a typical exemplary embodiment, the jaw parts of the forceps are suitable for receiving tool elements. The latter are preferably screwed to the jaw part in receptacles provided for this purpose and are therefore secured in the handle part and lever arm. By means of the screw connection, it is possible to exchange warn tool elements. Furthermore, there is the possibility of using different tool elements with the same forceps.

Tool elements are preferably used for cutting surgical implants, in particular titanium implants. Furthermore, tool elements are also conceivable and included here that are suitable for cutting wire or for bending, stamping, punching and/or pinching a very wide variety of workpieces and/or implants, also outside the medical sphere.

The tool elements for cutting surgical implants are suitable in conjunction with the high transmission ratio of the forceps for also cutting high-strength titanium implants. In order to make this easier, in a typical exemplary embodiment, at least one of the tool elements for cutting surgical implants has receiving pins. The shape, size and/or distance of the receiving pins is preferably adapted to the surgical implants to be cut. The receiving pins make it possible to secure the implant in the correct position between the tool elements.

In order to prevent bending of the implant at the designated cut edge during cutting, in one exemplary embodiment the tool elements have spring pressers. The latter are preferably composed of a firm, but nevertheless elastic and deformable medical silicone and press the implant to be cut onto the opposite tool element.

By means of the typical embodiment of the tool elements for cutting surgical implants, with the receiving pins and the spring pressers, and the virtually parallel arrangement of the tool elements, very neat guiding of the item for cutting can also be ensured. Furthermore, by means of the virtually parallel alignment of the tool elements in the open state, it is ensured that an item for cutting does not slide out of the cutting edges when the forceps are closed.

In a typical exemplary embodiment, the spring pressers are secured in the tool elements by the screws which secure the tool elements in the jaw parts of the handle part and of the lever arm. The spring pressers can therefore also be changed easily.

By means of the embodiment of the bearings as a type of rolling bearing, the pressure lever and the lever arm do not bear in the bearing surfaces in the open state of the forceps. The spring also lies loosely in the housing in the open state. Thus, in the open state, none of the individual components of the forceps is under tension. Since, in the wide open state, there are therefore no pressed-on surfaces, as in a conventional joint, the forceps can be sterily cleaned as a result without previous dismantling.

Since all of the connections of the forceps are designed to be releasable or plugged-in, the individual parts of the forceps can readily also be cleaned individually. It is also easily possible to interchange individual parts. This has the advantage that, in the event of a defect of an individual part, such as, for example, the spring, in the housing or of a spring presser in the tool elements, an entire new forceps does not have to be provided. Furthermore, the simple construction of the forceps enables the latter to be readily dismantled and reassembled by the medical personnel.

BRIEF DESCRIPTION OF THE DRAWINGS

Further advantages, features and details of the invention emerge from the following description of preferred exemplary embodiments and with reference to the drawings; in the latter FIG. 1 shows a typical embodiment of a forceps according to the invention with a closed jaw;

FIG. 2 shows the exemplary embodiment according to FIG. 1 without the housing cover and with a closed jaw;

FIG. 4 shows a side view of a handle part according to the invention of the forceps according to FIG. 1;

FIG. 5 shows a view from the proximal side of the handle part according to FIG. 4;

FIG. 6 shows a top view of the handle part according to FIG. 1;

FIG. 7 shows a side view of a pressure lever according to the invention of the forceps according to FIG. 1;

DETAILED DESCRIPTION

Figure 3:
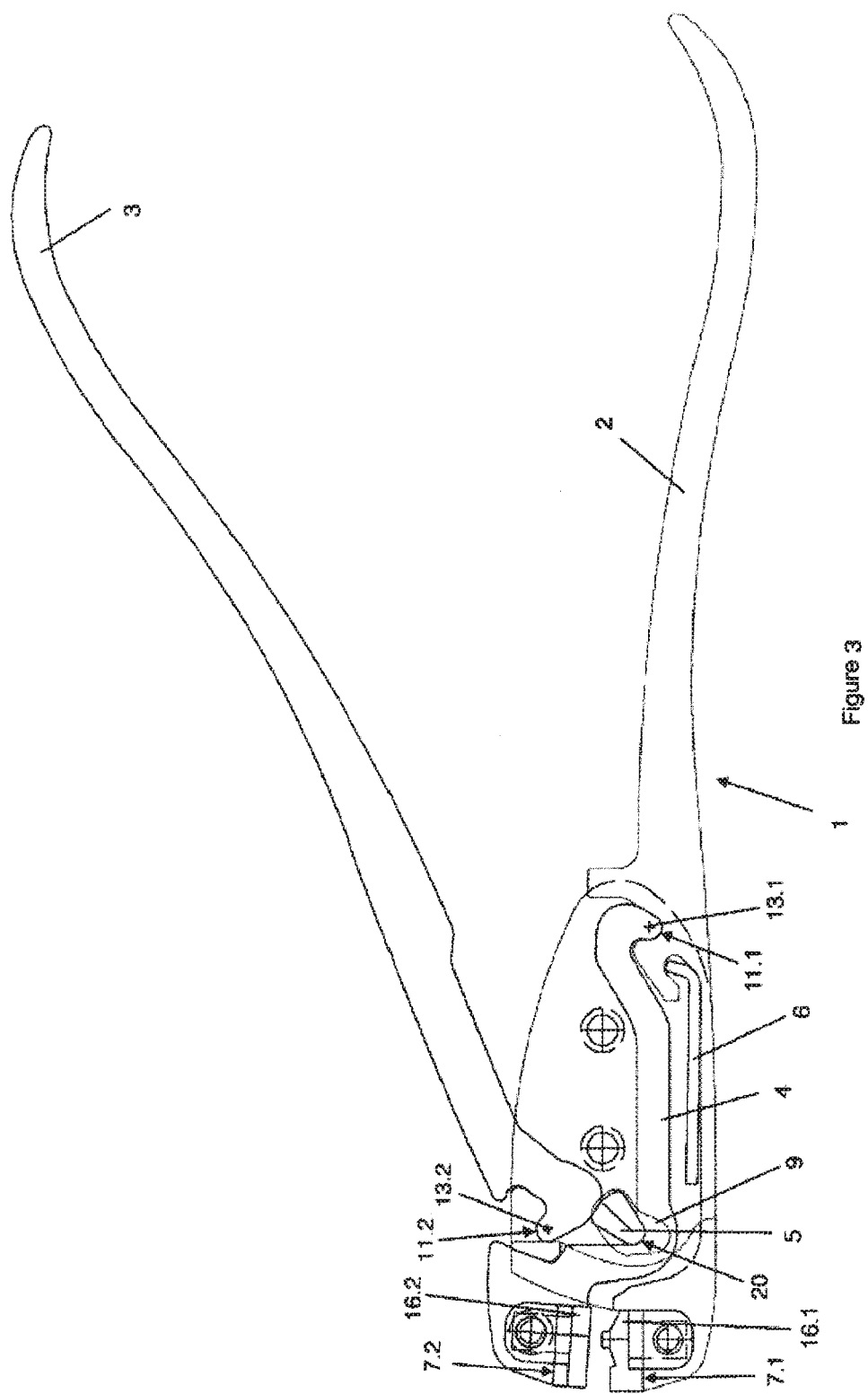
FIG. 3 shows the exemplary embodiment according to FIG. 2 with an open jaw.
Figures 8, 9:
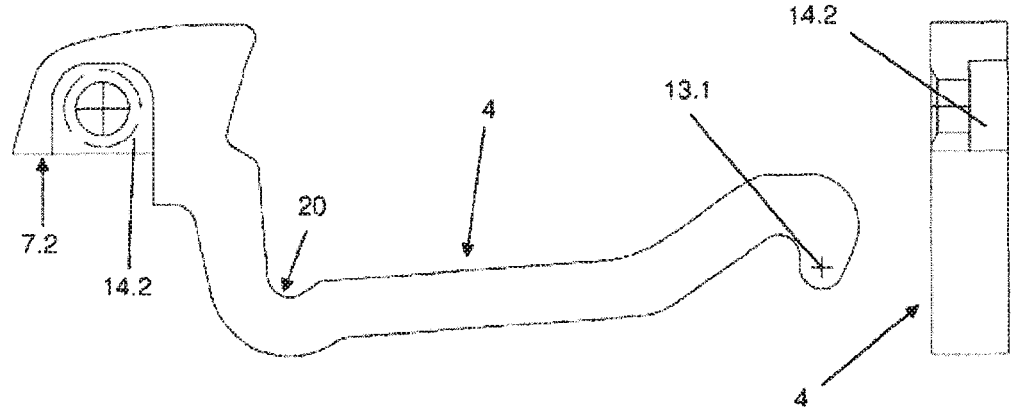
FIG. 8 shows a side view of a pressure lever according to the invention of the forceps according to FIG. 1.
FIG. 9 shows a view from the proximal side of the lever arm according to FIG. 8.

FIG. 1 shows a typical embodiment of a forceps 1 according to the invention with a closed jaw. A forceps according to the invention comprises here a pressure lever 3 next to a handle part 2 with a jaw part 7.1. Said pressure lever 3 is mounted pivotably in relation to the handle part 2.

FIG. 2 shows the forceps 1 according to FIG. 1 without a housing cover 8. A fulcrum/pivot point 13.2 about which the pressure lever 3, in a typical exemplary embodiment, turns or pivots is illustrated there. Said fulcrum/pivot point is located on that side of the pressure lever 3 which faces the jaw parts 7.1 and 7.2.

Furthermore, a forceps according to the invention comprises a lever arm 4 with a second jaw part 7.2. In a typical exemplary embodiment, said jaw part is arranged between the handle part 2 and the pressure lever 3 and can be pressurized by the pressure lever 3.

In FIG. 2, said lever arm 4 is illustrated in a state used in the forceps 1. It is furthermore shown that the lever arm 4 also has a fulcrum/pivot point 13.1 in relation to the handle part 2, about which the lever arm is mounted pivotably in relation to the handle part 2. Said fulcrum/pivot point 13.1 is located on that side of the lever arm 4 which faces away from the jaw part 7.2 in order to permit as high a transmission ratio as possible and, in addition, as parallel an arrangement as possible.

Furthermore, it can be gathered from FIG. 2 and FIG. 3, which shows the forceps 1 according to the invention without a housing cover 8 in the open state, that both the mounting between the pressure lever 3 and the handle part 2 and the mounting between the lever arm 4 and the handle part 2 involve a free mounting. This makes easy dismantling of the forceps 1 by a user possible.

Furthermore, it is shown in FIGS. 2 and 3 that a rolling body 5 is arranged between the pressure lever 3 and the lever arm 4. A compressive force exerted on the pressure lever 3 can be transmitted to the lever arm 4 via the rolling body 5.

Figures 10, 11:
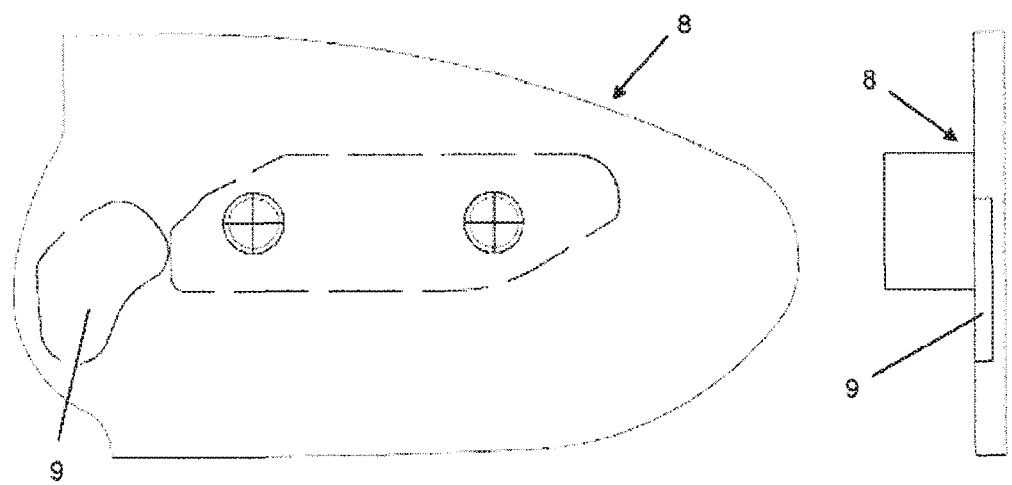
FIG. 10 shows a side view of a housing cover according to the invention of the forceps according to FIG. 1.
FIG. 11 shows a view from the proximal side of the housing cover according to FIG. 10.

In order to transmit this force from the pressure lever 3 to the lever arm 4 in as loss-free a manner as possible via the rolling body 5, the rolling body is guided in a slotted guide 9. For this purpose, the slotted guide 9 is provided in the handle part 2 and/or the housing cover 8. The handle part 2 and the position of the slotted guide in the handle part 2 are illustrated in more detail in FIGS. 4 and 6. The housing cover 8 and the position of the slotted guide 9 in the housing cover are illustrated in more detail in FIGS. 10 and 11. Furthermore, the lever arm 4 has a concave receptacle 20 for the rolling body 5, the receptacle likewise contributing to as loss-free a transmission force as possible. In order to assist a rolling movement, the concave receptacle 20 for the rolling body has, in a typical exemplary embodiment, an internal radius which is larger than the external radius of the rolling body 5 in the region of the rolling surface.

It is furthermore apparent from FIGS. 4, 5 and 6 that the handle part 2 at least partially has a housing which serves for receiving various individual parts of the forceps 1. The handle part 2 has a concave receptacle 11.2 on that side of the housing which faces the jaw part 7.1. The concave receptacle 11.2 is suitable for receiving the jaw-side end of the pressure lever 3 with the fulcrum/pivot point 13.2. In a typical exemplary embodiment, the concave receptacle 11.2 has an internal radius which is larger than the external radius of the pressure lever 3 about the fulcrum/pivot point 13.2.

The handle piece 2 has a further concave receptacle 11.1 on that side of the housing which faces away from the jaw part 7.1. The receptacle 11.1 is suitable for receiving that end of the lever arm 4 which is opposite the jaw part 7.2 and has the fulcrum/pivot point 13.1. In a typical exemplary embodiment, the concave receptacle 11.1 has an internal radius which is larger than the external radius of the lever arm 4 about the fulcrum/pivot point 13.1.

Furthermore, on that side of the housing which faces the jaw part 7.1, the handle part 2 has a recess which is suitable for accommodating the lever arm 4. In a typical exemplary embodiment, the recess for receiving the lever arm 3 is designed in the form of a closed channel 10 in the direction of a longitudinal axis L of the handle part 2. When the forceps 1 is assembled, the lever arm 4 is therefore introduced into the closed channel 10 from the jaw side.

Furthermore, the handle part 2 has a hook-in recess 12 for a spring 6, which hook-in recess is suitable for bringing the forceps 1 from a use position with a closed jaw into a use position with an open jaw. The housing of the forceps 1, which housing is at least partially formed by the handle part 1, is, as illustrated in FIG. 1, closed by the housing cover 8. A fixed connection of the handle part to the housing cover can take place here via screws and/or a plug-in connection.

The connection preferably takes place via screws which are not illustrated specifically in the figures.

Figure 12:
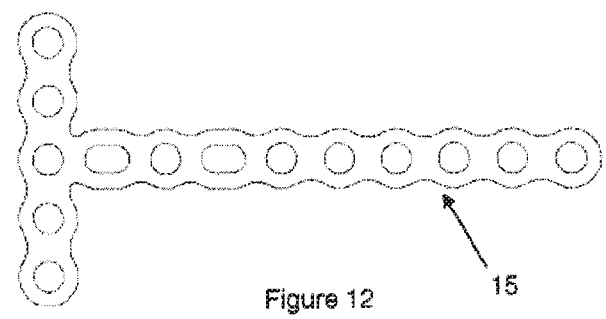
FIG. 12 shows a typical exemplary embodiment of a surgical implant.
Figure 14:
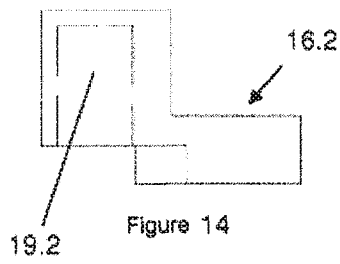
FIG. 14 shows a front view of the tool element according to FIG. 13.
Figure 13:
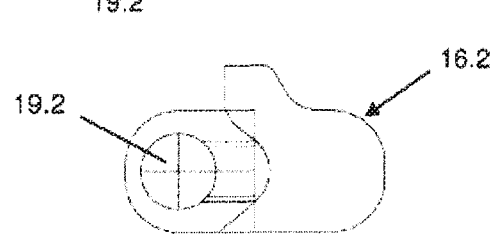
FIG. 13 shows a top view of a tool element for the lever arm of a forceps according to the invention.
Figure 15:
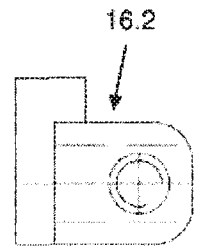
FIG. 15 shows a side view of the tool element according to FIG. 13.

In an embodiment according to the invention of the forceps, the jaw parts 7.1 and 7.2 of the forceps 1 are also aligned virtually parallel to each other in the open state. Furthermore, the jaw parts 7.1 and 7.2 are suitable for receiving tool elements 16.1 and 16.2. In a typical exemplary embodiment, the tool elements 16.1 and 16.2 are exchangeable. The tool elements 16.1 and 16.2 are preferably inserts which are suitable for cutting surgical implants 15. FIG. 12 illustrates an embodiment of such an implant 15. A sufficiently high transmission ratio in order even to cut high-strength titanium implants is achieved by the arrangement of the fulcrum/pivot points 13.1 and 13.2.

In an embodiment according to the invention of the forceps 1, the tool elements 16.1 and 16.2 are secured by screw connections in the receptacles 14.1 and 14.2 which are arranged in the jaw parts 7.1 and 7.2 of the handle part 2 and of the lever arm 4. In order neatly and effectively to sever the surgical implant 15, in a typical exemplary embodiment the cutting edges of the tool elements 16.1 and 16.2 are adapted to each other and to the surgical implant 15.

Figure 17:
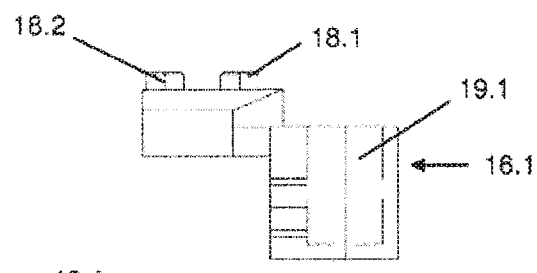
FIG. 17 shows a front view of the tool element according to FIG. 16.
Figure 16:
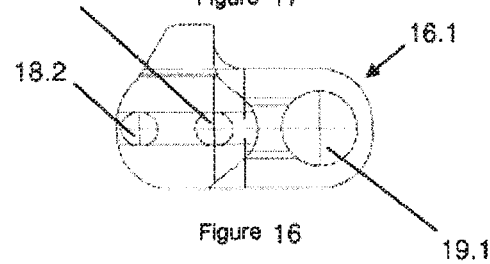
FIG. 16 shows a top view of a tool element for the handle part of a forceps according to the invention.
Figure 18:
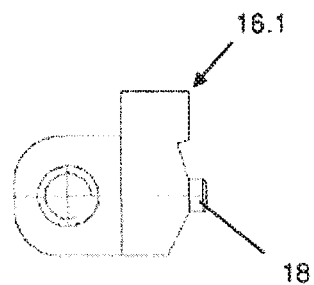
FIG. 18 shows a side view of the tool element according to FIG. 16.

Furthermore, as illustrated in FIGS. 16 to 18, at least one of the tool elements 16.1 and/or 16.2 has receiving pins 18.1 and 18.2 which prevent slipping of the surgical implant 15 and therefore secure the surgical implant 15. Furthermore, it can be ensured by the receiving pins 18.1 and 18.2 that the web width at the cut edge of the surgical implant 15 has adequate strength.

Figure 19:
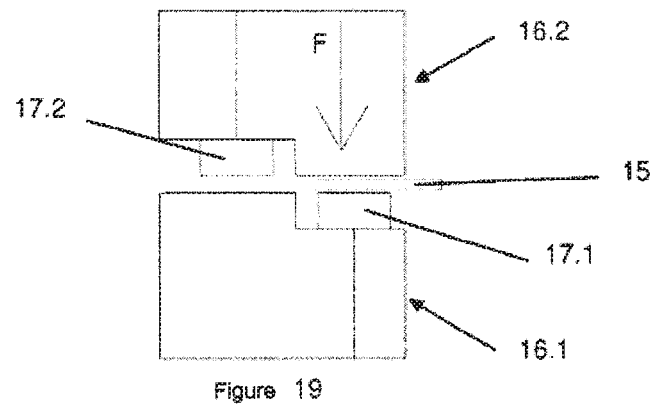
FIG. 19 shows a cutting pattern of the tool elements for an implant.

In a typical exemplary embodiment, the tool elements 16.1 and 16.2 also have recesses which serve as receptacles 19.1 and 19.2 for spring pressers 17.1 and 17.2. The spring pressers 17.1 and 17.2 prevent the implant 15 from bending during cutting. This is illustrated in FIG. 19 which shows the cutting pattern for a typical exemplary embodiment.

In order to enable the jaw of the forceps 1 to completely close, the spring pressers 17.1 and 17.2 are preferably produced from a firm, but elastic and therefore deformable silicone. In a typical exemplary embodiment, the spring pressers 17.1 and 17.2 are secured in the tool elements 16.1 and 16.2 by the screw connections which secure the tool elements 16.1 and 16.2 in the receptacles 14.1 and 14.2 of the jaw parts 7.1 and 7.2.

The operation of the forceps 1 with tool elements 16.1 and 16.2 for cutting surgical implants 15 is illustrated below. The tool elements 16.1 and 16.2 for cutting surgical implants are illustrated in FIGS. 14 to 18. The associated cutting pattern is illustrated in FIG. 19:

In order to cut an implant 15, the latter is inserted into the open jaw of the forceps 1. By means of the receiving pins 18.1 and 18.2, as ideal a positioning of the implant 15 as possible between the tool elements 16.1 and 16.2 in the jaw part of the forceps 1 is achieved.

By exertion of a force on the pressure lever 3, the latter pivots about the fulcrum/pivot point 13.2 and exerts a force on the rolling body 5. The latter is thereby guided in the slotted groove 9 in the direction of the lever arm 4. As a result, the lever arm 4 begins to pivot about the fulcrum/pivot point 13.1. The jaw part 7.2 of the lever arm 4 thereby moves in the direction of the jaw part 7.1 of the handle part 2.

The implant 15 is secured between the tool elements 16.1 and 16.2 by the spring pressers 17.1 and 17.2 and the receiving pins 18.1 and 18.2. By means of the compression, a force F then acts on the implant 15 and the latter is thereby severed at the designated cut edge.

The invention claimed is:

1. A surgical forceps (1) comprising at least one handle part (2) and a pressure lever (3) which is mounted pivotably relative to the handle part, and further comprising a jaw consisting of two jaw parts (7.1, 7.2), wherein one of the jaw parts (7.1) is provided on the handle part (2) and wherein a lever arm (4) which has the second jaw part (7.2) and is pressurized by the pressure lever (3) is arranged between the handle part (2) and the pressure lever (3) and the lever arm (4) is mounted pivotably in relation to the handle part (2), wherein a rolling body (5) is arranged between the pressure lever (3) and the lever arm (4) and a force exerted on the pressure lever (3) is transmitted via the rolling body (5) to the lever arm (4), the rolling body (5) is guided in a slotted guide (9), the slotted guide (9) for guiding the rolling body (5) is provided in the handle part (2) and/or in a housing cover (8) and the lever arm (4) has a concave receptacle (20) for the rolling body (5) with an internal radius which is larger than an external radius of the rolling body (5) in the region of the rolling surfaces, wherein, by exerting a force on the pressure lever (3), the latter pivots about a fulcrum/pivot point (13.2) and exerts a force on the rolling body (5) which is guided in the slotted guide (9) in the direction of the lever arm (4), as a result of which the lever arm (4) begins to pivot about a fulcrum/pivot point (13.1) and the jaw part (7.2) of the lever arm (4) moves in the direction of the jaw part (7.1) of the handle part (2), and the mounting between handle part (2) and pressure lever (3) and between the handle part (2) and the lever arm (4) is a free mounting.

2. The forceps (1) as claimed in claim 1, wherein a fulcrum/pivot point (13.1) of the lever arm (4) is located on a side facing away from the jaw part (7.2).

3. The forceps (1) as claimed in claim 1, wherein a fulcrum/pivot point (13.2) of the pressure lever (3) is located on a side of the pressure lever (3) which faces the jaw parts (7.1, 7.2).

4. The forceps (1) as claimed in claim 1, wherein the handle part (2) is at least partially a part of a housing.

5. The forceps (1) as claimed in claim 1, wherein the handle part (2) has, at a jaw-side end, a concave receptacle (11.2) for the pressure lever (3).

6. The forceps (1) as claimed in claim 1, wherein the handle part (2) has, at an end facing away from the jaw, a concave receptacle (11.1) for the lever arm (4).

7. The forceps (1) as claimed in claim 1, wherein the handle part (2) has, at the jaw-side end, a recess which is suitable for receiving the lever arm (4).

8. The forceps (1) as claimed in claim 7, wherein the recess for receiving the lever arm (4) is designed as a closed channel (10) in the direction of a longitudinal axis (L) of the handle part (2).

9. The forceps (1) as claimed in claim 1, wherein the handle part (2) has a hook-in recess (12) which is suitable for receiving a spring (6).

10. The forceps (1) as claimed in claim 1, wherein the housing cover (8) is suitable for closing the housing.

11. The forceps (1) as claimed in claim 1, wherein the jaw parts (7.1, 7.2) are aligned substantially parallel to each other.

12. The forceps (1) as claimed in claim 1, wherein the jaw parts (7.1, 7.2) are suitable for receiving tool elements (16.1, 16.2) which are exchangeable.

13. The forceps (1) as claimed in claim 12, wherein at least one of the tool elements (16.1, 16.2) for cutting implants has receiving pins (18.1, 18.2) for receiving and securing the implant (15).

14. The forceps (1) as claimed in claim 13, wherein the tool elements (16.1, 16.2) for cutting implants (15) have spring pressers (17.1, 17.2).

15. The forceps (1) as claimed in claim 14, wherein the spring pressers (17.1, 17.2) are secured in the tool elements (16.1, 16.2) for cutting implants (15) by means of screws in the tool elements (16.1, 16.2), which screws secure the tool elements (16.1, 16.2) in the handle part (2) and/or lever arm (4).

\* \* \* \* \*